US010201561B2

(12) United States Patent
Watanabe et al.

(10) Patent No.: US 10,201,561 B2
(45) Date of Patent: Feb. 12, 2019

(54) ANTIVIRAL FIBER ASSEMBLY WITH CELLULOSE SULFATE

(75) Inventors: Yoshiko Watanabe, Osaka (JP); Kazuyuki Sakamoto, Osaka (JP)

(73) Assignees: ES FiberVisions CO., LTD., Osaka (JP); ES FiberVisions Hong Kong Limited, Kowloon, Hong Kong (CN); ES FiberVisions LP, Athens, GA (US); ES FiberVisions ApS, Varde (DK)

( * ) Notice: Subject to any disclaimer, the term of this patent is extended or adjusted under 35 U.S.C. 154(b) by 0 days.

(21) Appl. No.: 13/266,660

(22) PCT Filed: Apr. 30, 2010

(86) PCT No.: PCT/JP2010/057986
§ 371 (c)(1),
(2), (4) Date: Oct. 27, 2011

(87) PCT Pub. No.: WO2010/126173
PCT Pub. Date: Nov. 4, 2010

(65) Prior Publication Data
US 2012/0058339 A1 Mar. 8, 2012

(30) Foreign Application Priority Data

Apr. 30, 2009 (JP) ................. 2009-111204

(51) Int. Cl.
D02G 3/00 (2006.01)
A61K 31/717 (2006.01)
A01N 43/16 (2006.01)
D06M 15/05 (2006.01)
D06M 15/055 (2006.01)
D06M 16/00 (2006.01)
A61L 2/23 (2006.01)

(52) U.S. Cl.
CPC ............ A61K 31/717 (2013.01); A01N 43/16 (2013.01); D06M 15/05 (2013.01); D06M 15/055 (2013.01); D06M 16/00 (2013.01); A61L 2/23 (2013.01); Y10T 428/2933 (2015.01)

(58) Field of Classification Search
USPC ....................................................... 428/375
See application file for complete search history.

(56) References Cited

U.S. PATENT DOCUMENTS

| 5,667,684 | A | 9/1997 | Motomura et al. |
| 2003/0181415 | A1* | 9/2003 | Zaneveld ............ A61K 9/0034 514/54 |
| 2004/0063597 | A1* | 4/2004 | Adair et al. ................. 510/276 |
| 2005/0172968 | A1 | 8/2005 | Hishida |
| 2008/0028986 | A1* | 2/2008 | Futterer et al. .......... 106/287.23 |
| 2008/0131454 | A1 | 6/2008 | Grassauer et al. |
| 2009/0105679 | A1* | 4/2009 | Joubert et al. ........... 604/385.01 |
| 2010/0040658 | A1 | 2/2010 | Grassauer et al. |
| 2010/0055060 | A1 | 3/2010 | Yoshida et al. |
| 2010/0330140 | A1 | 12/2010 | Stewart et al. |
| 2011/0110818 | A1 | 5/2011 | Mowbray-d'Arbela et al. |
| 2012/0315331 | A1 | 12/2012 | Pettersson et al. |

FOREIGN PATENT DOCUMENTS

| EP | 0679436 | 4/1995 |
| JP | 07-289891 | 11/1995 |
| JP | 11-019238 | 1/1999 |
| JP | 2000-328448 | 11/2000 |
| JP | 2002-338481 | 11/2002 |
| JP | 2004-330543 | 11/2004 |
| JP | 2005-112748 | 4/2005 |
| JP | 2006-187508 | 7/2006 |
| JP | 2006-274245 | 10/2006 |
| JP | 2008-535955 | 9/2008 |
| JP | 2008-229435 | 10/2008 |
| JP | 2008-266265 | 11/2008 |
| JP | 2010-512307 | 4/2010 |
| WO | WO2007112966 A1 * | 10/2007 |
| WO | 2008/066193 | 6/2008 |
| WO | 2009/003057 | 12/2008 |
| WO | 2009/158527 | 12/2009 |

* cited by examiner

Primary Examiner — Vincent Tatesure
(74) Attorney, Agent, or Firm — Hamre, Schumann, Mueller & Larson, P.C.

(57) ABSTRACT

An object of the present invention is to provide an antiviral fiber assembly in which an antiviral agent is retained with chemical stability over a long period of time, and which is gentle to the human body. A further object of the present invention is to provide a fiber assembly with cellulose sulfate that can exhibit sufficient antiviral activity over a long period of time. Further, another object of the present invention is to provide a textile product obtained using such a fiber assembly.

The present invention provides a fiber assembly with cellulose sulfate, wherein the hyaluronidase inhibitory activity is 50% or higher; and a process for producing a fiber assembly with cellulose sulfate, including treating a fiber assembly with an aqueous cellulose sulfate solution and drying, then treating the same with a pH buffer solution and drying.

8 Claims, No Drawings

ANTIVIRAL FIBER ASSEMBLY WITH CELLULOSE SULFATE

TECHNICAL FIELD

The present invention relates to a fiber assembly exhibiting antiviral properties, and more particularly to an antiviral fiber assembly having cellulose sulfate deposited thereon. The present invention also relates to a textile product obtained using such a fiber assembly.

BACKGROUND ART

Several fiber assemblies with antiviral properties have been proposed in the past.

For example, Patent document 1 proposes a fiber containing an antimicrobial agent consisting of a silver salt or iodine complex salt, and Patent document 2 proposes a product (mask) wherein silver is plated or vapor-deposited onto the surface of a synthetic fiber. Patent document 3 lists an example wherein an antiviral agent with a phenolic hydroxyl group is used as an antimicrobial agent. Patent document 4 lists an example wherein a nitrogen-containing nonionic surfactant and a benzoic ester are used on fibers, etc., as an antimicrobial agent.

Although a metal ion is used in some fiber assemblies with antiviral properties, some such fiber assemblies can cause a metal sensitivity reaction. Therefore, it is necessary to develop a fiber assembly with antiviral properties that is gentle to the human body because it utilizes an antiviral agent with weak cytotoxicity and regardless of the user does not cause an allergic reaction.

Problems must also be solved such as the fact that if an antiviral agent is simply applied to a fiber assembly, it does not adhere uniformly, and it cannot be stably retained thereon.

[Patent document 1] Japanese Patent Application Publication No. 2002-338481
[Patent document 2] Japanese Patent Application Publication No. H11-019238
[Patent document 3] Japanese Patent Application Publication No. 2005-112748
[Patent document 4] Japanese Patent Application Publication No. 2006-187508

DISCLOSURE OF THE INVENTION

An object of the present invention is to provide an antiviral fiber assembly in which an antiviral agent is retained with chemical stability over a long period of time, and which is gentle to the human body. A further object of the present invention is to provide a fiber assembly with cellulose sulfate that can exhibit sufficient antiviral activity over a long period of time. A further object the present invention is to provide a textile product obtained using the aforementioned fiber assembly that can exhibit sufficient antiviral activity over a long period of time.

After diligent investigation to solve the aforementioned problems, the inventors successfully arrived at a fiber assembly that retains cellulose sulfate effectively and that can exhibit sufficient antiviral activity over a long period of time.

Therefore, the constituent features of the present invention are as follows:

(1) A fiber assembly with cellulose sulfate, wherein the hyaluronidase inhibitory activity is 50% or higher;

(2) The fiber assembly of (1) above, wherein fibers constituting the aforementioned fiber assembly are hydrophilic fibers or hydrophilized fibers;

(3) The fiber assembly of (2) above, wherein the hydrophilized fibers are obtained by hydrophilization of hydrophobic fibers;

(4) The fiber assembly of (1) above, wherein cellulose sulfate is retained on a fiber assembly that has undergone a hydrophilization treatment;

(5) The fiber assembly of any one of (2) to (4) above, wherein the hydrophilization treatment is a surfactant treatment;

(6) The fiber assembly of any one of (1) to (5) above, wherein a treatment with a pH buffer solution is performed;

(7) The fiber assembly of any one of (1) to (6) above, wherein fibers constituting the fiber assembly comprise polyolefin and/or polyester;

(8) A textile product obtained using the fiber assembly of any one of (1) to (7) above;

(9) A process for producing a fiber assembly with cellulose sulfate including:
    treating a fiber assembly with an aqueous cellulose sulfate solution and drying; and then
    treating them with a pH buffer solution and drying; and

(10) The process for producing a fiber assembly of (9) above, including treating the fiber assembly with a surfactant before treating the same with the aqueous cellulose sulfate solution.

A sufficient amount of cellulose sulfate is retained uniformly and sufficiently on the fiber assembly of the present invention, and thereby the fiber assembly of the present invention can exhibit antiviral activity by cellulose sulfate. Moreover, the fiber assembly of the present invention is an antiviral fiber assembly that is gentle to the human body.

Especially in the case that the fiber assembly of the present invention is treated with a pH buffer, the cellulose sulfate can be retained thereon with chemical stability over a long period of time, and thus can exhibit antiviral activity over a long period of time. Because the fibers of the fiber assembly of the present invention are either hydrophilic or are imparted with hydrophilicity by treatment with a surfactant, for example, the cellulose sulfate and pH buffer solution can be retained uniformly thereon, and antiviral activity can be exhibited uniformly and sufficiently thereby.

By using the production process for the fiber assembly with cellulose sulfate of the present invention, the cellulose sulfate can be retained uniformly on the fiber assembly, and moreover the cellulose sulfate can be retained on the fiber assembly with chemical stability over a long period of time. Thus, in accordance with the fiber assembly production process of the present invention, the cellulose sulfate can be retained on the fiber assembly uniformly and stably for a long period of time, thereby making it possible to provide a fiber assembly that exhibits sufficient antiviral activity.

MODE FOR CARRYING OUT THE INVENTION

In the present invention the fiber assembly refers to a web, nonwoven fabric, woven fabric, tow fabric, etc. Such a fiber assembly is one that is produced from fibers by conventional methods.

The optimal amount of cellulose sulfate adhering to the fiber assembly can be determined indirectly by using the hyaluronidase inhibitory activity method. The hyaluronidase inhibitory activity method verifies the presence of sulfate groups. In the present invention, the antiviral activity exhibited by the fiber assembly is evaluated using the value of hyaluronidase inhibitory activity measured by the hyaluronidase inhibitory activity method as an indicator.

For practical purposes, a hyaluronidase inhibitory activity value of 50% or higher is preferred for expressing the effectiveness of the cellulose sulfate in the present invention. Cellulose sulfate is known to have antiviral properties, and a fiber assembly with cellulose sulfate at an effective dose can be expected to provide satisfactory antiviral activity. Herein the concept of effective dose of cellulose sulfate refers to one with a hyaluronidase inhibitory activity value of 50% or higher.

Examples of nonwoven fabric include through-air nonwoven fabric, spunbond nonwoven fabric, melt-blown nonwoven fabric, etc. Spunbond nonwoven fabric is particularly preferred because the cellulose sulfate easily adheres uniformly to the nonwoven fabric. Because spunbond nonwoven fabric is thinner than through-air nonwoven fabric and melt-blown nonwoven fabric, and because the distance between the fibers thereof is intermediate between the other two, it is believed that the aqueous cellulose sulfate solution penetrates the fabric easily, and that the cellulose sulfate itself does not easily become detached therefrom.

When retaining cellulose sulfate on a fiber assembly, it is preferable for the fiber assembly to be constituted by either hydrophilic fibers or hydrophilized fibers, or for the fiber assembly to undergo a hydrophilization treatment. Moreover, when retaining cellulose sulfate on a fiber assembly, in addition to using a fiber assembly constituted by either hydrophilic fibers or hydrophilized fibers, one also can perform a hydrophilization treatment on the fiber assembly itself, or one can use a fiber assembly constituted by hydrophobic fibers upon which a hydrophilization treatment has been performed.

When the fiber assembly of the present invention is constituted by hydrophilic fibers, examples of such hydrophilic fibers include cotton, pulp, tissue, etc.

The fiber assembly of the present invention can also be constituted by hydrophilized fibers. Herein, the term hydrophilized fibers refers to hydrophobic fibers wherein a hydrophilization treatment has been performed.

Examples of a hydrophilization treatment on fibers and a hydrophilization treatment on a fiber assembly include a sulfonation treatment, fluorine gas treatment, surface activation treatment, etc.

Crystalline thermoplastic resins such as polyolefin, polyester, or a mixture thereof can be listed as examples of a component used for a hydrophobic fiber. Among the crystalline thermoplastic resins, a fiber constituted by polyolefin and/or polyester is preferable as the hydrophobic fiber from the standpoint of workability and strength. The fiber can be a monocomponent fiber, or it can be a multiple component fiber comprising two or more types thereof. A conjugate fiber can be listed as an example of a multiple component fiber. Examples of the conjugate fiber include a concentric sheath-core type, eccentric sheath-core type, side-by-side type, radial form, etc., and it can have a circular cross section or a non-circular cross section. Examples of specific resin compositions include combinations of high-density polyethylene/polypropylene, low-density polyethylene/polypropylene, high-density polyethylene/polyethylene terephthalate, low-density polyethylene/polyethylene terephthalate, polypropylene/polyethylene terephthalate, etc.

The hydrophilization of hydrophobic fibers, e.g., surface activation treatment by a surfactant, can be carried out by attaching a fiber treatment agent (also called a textile oil) containing a conventionally used surfactant to the fibers after spinning. The treatment by a surfactant can also be performed by attaching the surfactant through immersion of the fiber assembly in an aqueous solution of the surfactant or by coating or spraying such a solution onto the fibers and/or fiber assembly.

Examples of surfactants used in surface activation treatments include anionic surfactants, amphoteric surfactants, nonionic surfactants, etc.

Among these types of surfactants, anionic surfactants are preferred from the standpoint that that the cellulose sulfate can be efficiently attached thereby, thus enhancing the hyaluronidase inhibitory activity. Examples of anionic surfactants include at least one type of anionic surfactant selected from a group consisting of carboxylates, sulfonates, sulfates, and phosphates. Phosphates, and specifically higher alcohol phosphates, are particularly preferred. Additionally, anionic surfactants can include higher alcohol phosphate monoester salts (e.g., a higher alcohol phosphate monoester disodium salt), higher alcohol phosphate diester salts (e.g., a higher alcohol phosphate diester sodium salt), an ethylene oxide adduct-higher alcohol phosphate ester salt, etc.

More specific examples include a $C_{8-12}$ phosphate ester salt, e.g., octyl phosphate salt ($C_8$), and dodecyl phosphate salt ($C_{12}$). Examples of preferred metal phosphate salts include the potassium salt, sodium salt, etc.

In relation to the total weight of the fiber assembly, a surfactant attached in a range of 0.2 to 2.0 wt % is preferred, and a surfactant attached in a range of 0.3 to 0.6 wt % is even more preferred from the standpoint of imparting hydrophilicity to the fiber assembly.

In particular, an anionic surfactant attached within a range of 0.2 to 2.0 wt % is preferred, and one within a range of 0.3 to 0.6 wt % is even more preferred. At that time, another surfactant such as a nonionic surfactant, etc., can be used concurrently in addition to the anionic surfactant. A cationic surfactant can also be used concurrently as a surfactant to be attached to the fibers within a range such that the effect of the present invention is not lost.

A commercially marketed surfactant satisfying the above conditions can be selected as a textile oil and can be attached to the fibers by a conventional method.

In the process of immersing the fiber assembly using an aqueous solution of surfactant, or of coating or spraying the fibers and/or fiber assembly with that solution, the concentration of surfactant in the aqueous solution can be suitably selected to satisfy the above conditions.

After the fibers and/or fiber assembly has been treated with the surfactant, it is preferably dried under suitable conditions (temperature, time, etc.)

A fiber assembly constituted by the above hydrophilic fibers, a fiber assembly constituted by fibers that have been hydrophilized, and/or a fiber assembly that has been hydrophilized (e.g., by treatment with a surfactant) as described above can be treated with cellulose sulfate, and the cellulose sulfate can be retained on the fiber assembly thereby.

The cellulose sulfate used in the present invention is not particularly limited herein, and for example, the cellulose sulfate disclosed in Japanese Patent Application Publication No. 2008-266265 can be used therefor. For example, cellulose sulfate marketed by Chisso Corporation as "SS-Cellulose" or by Acros Organics as "Cellulose sulfate, sodium salt" can be used. The cellulose sulfate of the former was described as having reduced cytotoxicity in Japanese Patent Application Publication No. 2008-266265, and the use thereof is preferred because it can be used safely with the human body. Provided the cellulose sulfate is easily soluble in water, the sizes and shapes of the particles are not limited, or it can be a powder, and the other properties thereof are not particularly limited herein. The preferred cellulose sulfate is one wherein 6 to 100% of the cellulose hydroxyl groups are sulfated and the weight-average molecular weight (Mw) lies within the range of 1 KDa to 1000 KDa. This degree of sulfur esterification of the cellulose sulfate amounts to a sulfur concentration of 13 to 17 wt % in relation to the total cellulose sulfate. The weight-average molecular weight is measured by gel permeation chromatography (GPC), and preferably is 50,000 to 100,000 (50 KDa to 100 KDa). One example is a cellulose sulfate that is a colorless powder with a sulfur content of 14 wt % and a weight-average molecular weight of about 66,000.

In the fiber assembly of the present invention it is preferable that at least part of the cellulose sulfate be exposed to the fiber surface and retained thereon. Such a configuration can be suitably obtained by a method wherein the cellulose sulfate is retained on the surfaces of the fibers of the fiber assembly.

Examples of methods whereby the cellulose sulfate is retained on the surface of the fiber assembly include a method wherein the fiber assembly is immersed in an aqueous solution of cellulose sulfate, a method wherein the cellulose sulfate is attached to the fiber assembly by spraying, and the like. From the standpoint of retaining the cellulose sulfate uniformly extending into the interior of the fiber assembly, preferably the fiber assembly is immersed in the aqueous solution of cellulose sulfate and then the entire aqueous solution is dried while the fiber assembly is permeated thereby. The drying temperature can be a temperature within a range such that the capability of the cellulose sulfate is not lost, and the fiber assembly can be suitably dried at a temperature of 80 to 100° C. depending on the drying time. The concentration of the cellulose sulfate in the aqueous solution of cellulose sulfate to be used can be suitably established in accordance with the intended antiviral activity of the fiber assembly, or as noted above, preferably after considering a mode wherein all of the aqueous solution has permeated into the fiber assembly.

From the viewpoint of retaining the cellulose sulfate in the fiber assembly stably for a long period of time, it is preferable to attach a pH buffer solution to the fiber assembly of the present invention. Means whereby the fiber assembly is treated with a pH buffer solution can be noted for attaching the pH buffer.

The effectiveness of the cellulose sulfate can be maintained well by attaching the solids of the pH buffer solution (hereinafter, buffer components) to the fiber assembly. The pH buffer solution provides a pH stabilizing effect, and therefore a pH buffer solution of about pH 6.4 can be specifically noted.

Attachment of the pH buffer solution to the fiber assembly exhibits the effect of protecting the cellulose sulfate from hydrolysis. Examples of the pH buffer solution include a citrate buffer solution, phosphate buffer solution, and the like. The buffer components of the citrate buffer are generally citric acid monohydrate+trisodium citrate dihydrate, and the buffer components of the phosphate buffer are generally sodium dihydrogen phosphate+disodium hydrogen phosphate.

The pH buffer solution (aqueous solution) can be attached to the fiber assembly by a method such as spraying or immersion, etc. The concentration of solids in the pH buffer solution is not limited herein, but a range of 0.1 to 0.5 wt % is suitable. With regard to the amount of buffer components attached to the fiber assembly, a range of 0.1 to 0.2 wt % in relation to the total weight of the fiber assembly is suitable.

The pH buffer solution can be attached to the fiber assembly simultaneously with, before, or after the cellulose sulfate is retained thereon. From the standpoint of protecting the cellulose sulfate from hydrolysis, preferably the pH buffer solution is attached after the cellulose sulfate has been retained thereon. When attaching the pH buffer solution simultaneously with the cellulose sulfate, it is preferable that the mass ratio of buffer components and cellulose sulfate (mass of buffer components/mass of cellulose sulfate) be in the range of 10 to 40 because the cellulose sulfate can be protected from hydrolysis thereby.

When attaching the pH buffer solution, it is believed that the buffer ingredients can be contained uniformly in the fiber assembly preferably by selecting a mode wherein all of a predetermined weighed out amount of pH buffer solution is impregnated in the fiber assembly. The drying temperature after the pH buffer solution is attached is not particularly limited herein provided it is a temperature such that the properties of the cellulose sulfate are not lost in the event that the cellulose sulfate has already been attached.

A fiber assembly retaining the cellulose of the present invention can be manufactured in the manner described above.

Therefore, the present invention includes a method suited for a manufacturing process for a fiber assembly with cellulose sulfate, and such a method includes treating the fiber assembly with the pH buffer solution and drying the same after the fiber assembly has been treated with the cellulose sulfate solution and dried. Among such methods are modes that include treating the fiber assembly with a surfactant before treating the same with the cellulose sulfate aqueous solution.

The fiber assembly of the present invention can retain 50% or more of its hyaluronidase inhibitory activity, and preferably 60% or more, in a storage test wherein the fiber assembly is let stand in an environment of 50° C. and 65% RH for 1 month.

The fiber assembly of the present invention can contain additives such as silver, titanium oxide, etc., within a range that does not interfere with the effect of the cellulose sulfate.

A ventilation layer can be overlaid on at least one surface of the fiber assembly. Examples of a ventilation layer include a fiber web, nonwoven fabric, etc. Detachment of the cellulose sulfate from the fiber assembly can be prevented by making the same into a layered product.

Preferably an overlaying ventilation layer has a smaller interfiber distance than that of the fiber assembly. As properties sought in a ventilation layer, a fiber layer with a mass per unit area of 25 to 35 $g/m^2$ and a specific volume of about 10 $cm^3/g$ is desirable.

The fibers constituting the fiber assembly of the present invention can include a component on which the cellulose sulfate is adsorbed or to which the cellulose sulfate is bonded. Examples of a fiber material containing such a component include a modified polyolefin (content of modifying agent 0.05 to 2 mol/kg) that has been graft-polymerized by a vinyl monomer containing at least one unsaturated carboxylic acid or unsaturated carboxylic acid anhydride (hereinafter, these are also referred to as modifying agents). Preferably the modifying agents include one or more type selected from maleic anhydride, acrylic acid, or methacrylic acid. Detachment of the cellulose sulfate from the fiber assembly can be ameliorated by having the fibers comprise such a component into the raw material constituting at least the surface of the fiber.

The fibers constituting the fiber assembly of the present invention can be crimped or non-crimped. The mode of crimping is not particularly limited herein, but because the effect of enclosing the cellulose sulfate in the fiber assembly is enhanced and detachment of the cellulose sulfate is inhibited by fibers with spiral crimping, such a mode is particularly preferred. Preferably, the crimping of the fibers is 10 to 30 crimps/inch. Preferably, crimping is carried out on the fiber assembly after attachment of the cellulose sulfate.

The fiber assembly of the present invention can be processed into a variety of products. The fiber assembly of the present invention is most suitably used in applications such as a sanitary material for medical uses such as masks, gowns, surgical gowns, etc., that utilize the effect thereof, and in particular, the antiviral activity brought about by the cellulose sulfate.

EXAMPLES

The present invention is described in detail below through examples, but is by no means limited thereto. The evaluations in the examples were performed by the methods shown below.

(Hyaluronidase Inhibitory Activity Test)

First 5±0.2 mg of the test fiber or fiber assembly was placed in a screw-top test tube. Then 100 µL of deionized water and 225 µL of a mixture of hyaluronidase-0.1 M acetate buffer solution adjusted to 2.83 mg/mL and 0.1 M acetate buffer solution-0.3 M NaCl was added. The tube was shaken to mix the contents, and then let stand at 37° C. for 20 min. The volume ratio of the hyaluronidase-0.1 M acetate buffer solution to the 0.1 M acetate buffer solution-0.3 M NaCl was 1:8. Next 200 µL of hyaluronic acid-0.1 M acetate buffer solution was added, and the tube was shaken to mix the contents and let stand at 37° C. for 20 min. Next 100 µL each of aqueous 0.4 N NaOH solution and 0.8 M sodium borate solution was added, the tube was shaken to mix the contents, the cap was closed, and the tube was let stand at 100° C. for 3 min. After the tube was cooled about 30 sec, 3 mL of p-dimethylamino benzaldehyde was added, the tube was shaken to mix the contents, and then let stand at 37° C. for 20 min. Finally, the test fiber or fiber assembly was removed, and the absorbance was measured at 585 nm.

The hyaluronidase inhibition activity was calculated by the following formula.

Hyaluronidase inhibition activity (%)={(γ−α)−(β−α)/(γ−α)}×100

α: Absorption measured after performing the above procedure without adding the fiber or fiber assembly test sample and by adding 225 µL of deionized water and hyaluronic acid-0.1 M acetate buffer solution in place of the mixed solution of hyaluronidase-0.1 M acetate buffer solution and 0.1 M acetate buffer solution-0.3 M NaCl.

β: Absorption measured after performing the above procedure using the fiber or fiber assembly test sample.

γ: Absorption measured after performing the above procedure without adding the fiber or fiber assembly test sample.

The above test was performed again on the fiber assembly as a storage test after letting the fiber assembly stand in an environment at 50° C. and 65% RH for 1 month.

[Nonwoven Fabric Made with the Fiber] Preparation of Fiber Assembly for Retaining Cellulose Sulfate Two types of nonwoven fabrics were produced by the following processes and conditions.

(1) Through-air process (TA): Short fibers cut to 51 mm long and prepared using high-density polyethylene and polypropylene were used as the test fibers. The test fibers used are a conjugate fiber and the form is a concentric sheath-core type with a circular cross section. The test fibers were made into a carded web using a roller-carder test machine, and the carded web was processed into a nonwoven fiber with a mass per unit area of 22 g/m$^2$ and a specific volume of about 54 cm$^3$/g with a suction dryer. The processing temperature was 130° C.

(2) Spunbond process (SB): Spunbond processed EB3020 from Chisso Polypro Fiber Co., Ltd. were used. EB3020 is a nonwoven fabric of high-density polyethylene and polypropylene with a mass per unit area of 20 g/m$^2$ and a specific volume of 11 cm$^3$/g.

[Treatment Agents]

The compositions of various treatment agents (units: wt %) used in treatment examples 1 to 5 are shown in Table 1 below divided into surfactant-containing textile oils used for the hydrophilization treatment (A) and pH buffer solutions (B). As described below, the surfactant-containing textile oils (A) and the pH buffer solutions (B) were used separately, and Table 1 lists the total of the surfactant-containing textile oil and the pH buffer as 100 wt %.

Treatment examples 1 and 2 are cases wherein a surfactant-containing textile oil (A) and a pH buffer (B) were both used, and these show the percentage by weight of each component in relation to the total weight of (A) and (B) combined. Treatment examples 3 to 5 are cases wherein only a surfactant-containing textile oil (A) was used. In the following section entitled "Treatment of nonwoven fabric," a method is described wherein both (A) and (B) were separately attached in sequence as the method of treating the nonwoven fabric (treatment examples 1 and 2). Treatment examples 3-5 are cases wherein only (A) was used, and these show the percentage by weight of each component in relation to (A).

TABLE 1

| Treatment agent | Component | Treatment example 1 | 2 | 3 | 4 | 5 |
|---|---|---|---|---|---|---|
| (A) anionic surfactant-containing oil (a) | sorbitan monopalminate | 8 | 8 | 10 | — | — |
| | sorbitan esters of tallow fatty acid | 26.4 | 26.4 | 33 | — | — |
| | potassium dodecyl phosphate | 24.8 | 24.8 | 31 | — | — |
| | mixed potassium phosphates* | 20.8 | 20.8 | 26 | — | — |
| anionic surfactant-containing oil (b) | potassium octyl phosphate | — | — | — | 66 | — |
| | potassium dodecyl phosphate | — | — | — | 8 | — |
| | propylene glycol | — | — | — | 18 | — |
| | ethylene glycol monobutyl ether | — | — | — | 8 | — |
| cationic surfactant-containing oil | polyglycerol fatty acid ester | — | — | — | — | 28 |
| | polyether | — | — | — | — | 28 |
| | polyether esters | — | — | — | — | 20 |
| | alkyl imidazolium alkyl sulfate | — | — | — | — | 10 |
| | polyoxyalkylene-modified silicone | — | — | — | — | 9 |
| | ethylene oxide adduct of alkanol amide | — | — | — | — | 5 |
| (B) | phosphate buffer** | 20 | — | — | — | — |
| | citrate buffer*** | — | 20 | — | — | — |

*The mixed potassium phosphates is dipotassium tridecan-1-yl phosphate
**Phosphate buffer: pH 6.4 (value listed on reagent bottle), mixed reagent of potassium dihydrogen phosphate: 10 g/L and dipotassium hydrogen phosphate: 3.67 g/L. Shown as wt % of solid components.
***Citrate buffer: mixture of citric acid monohydrate and trisodium citrate dihydrate with weight ratio of 1:10 dissolved in deionized water and adjusted to a pH of 6.2. Shown as wt % of solid components.

[Treatment of Nonwoven Fabric]

A hydrophilization treatment and treatment with cellulose sulfate (treatment examples 1 to 5) were performed in the following sequence on nonwoven fabrics prepared as described above, and then a treatment with a pH buffer was performed (treatment examples 1 and 2). In treatment example 6 only a treatment with cellulose sulfate was performed on the nonwoven fabric.

First 3 g of the textile oil (A) of Table 1 diluted to have a solid component of 0.4 wt % was weighed out into a beaker so that the solid component would be 0.4 wt % in relation to the 3 g of nonwoven fabric that had been weighed out, and then deionized water was added and the volume was increased to make it sufficient to immerse the nonwoven fabric. Then the nonwoven fabric, which had been kept in a separate container, was immersed to attach the oil thereto. Rubber gloves were worn, and the nonwoven fabric was massaged with the hands to attach the oil uniformly to the nonwoven fabric. To attach surfactant that had become adhered to the walls of the beaker to the nonwoven fabric, a small amount of deionized water was swirled around the inside walls of the beaker and then attached to the nonwoven fabric in the manner described above. By repeating this procedure about two times, it was possible to attach essentially the entire amount of surfactant to the nonwoven fabric. The nonwoven fabric with the surfactant attached was placed on a Teflon® film, and dried for 40 min in a 90° C. constant temperature bath. The nonwoven fabric was turned over once after 20 min had elapsed.

Next, 3 g of cellulose sulfate diluted to have a solid component of 0.01 wt % was weighed out into a beaker so that the solid component would be 0.01 wt % in relation to the weight of the nonwoven fabric, and then the entire amount was attached and dried by the same method used for the textile oil described above. The cellulose sulfate was from Chisso Corporation (Lot No. A07070101). The cellulose sulfate was a colorless powder with a sulfur content of 14 wt % and a weight-average molecular weight of 66,000 (GPC measured value). The GPC measurement was performed as follows: GPC apparatus: Waters 2695, RI detector: Waters 2487, column: Shodex OHpak SB-G+OHpak SB-805 HQ+OHpak SB-802.5 HQ.

Finally, 3 g of pH buffer solution (B) diluted in deionized water to have a solid component of 0.1 wt % was weighed out into a beaker so that the solid component (as solid component of pH buffer solution) would be 0.1 wt % in relation to the weight of the nonwoven fabric, and then the entire amount was attached and dried by the same method used for the textile oil and cellulose sulfate described above.

Treatment examples 1 to 6 and the test results are described below.

[Treatment Example 1]

A spunbond nonwoven fabric was treated with a textile oil containing potassium dodecyl phosphate and mixed potassium phosphates as anionic surfactants, and sorbitan monopalminate and sorbitan esters of tallow fatty acid as nonionic surfactants, and after the cellulose sulfate was attached, the fabric was treated with a phosphate buffer solution.

The results of the hyaluronidase inhibitory activity test revealed that both before and after storage the inhibitory activity was 50% or higher. A fiber assembly that achieves the object of the present invention was obtained thereby.

[Treatment Example 2]

A spunbond nonwoven fabric was treated with a textile oil containing potassium lauryl phosphate and mixed potassium phosphates as anionic surfactants, and sorbitan monopalminate and sorbitan esters of tallow fatty acid as nonionic surfactants, and after the cellulose sulfate was attached, the fabric was treated with a citrate buffer solution.

The results of the hyaluronidase inhibitory activity test revealed that both before and after storage the inhibitory activity was 50% or higher. A fiber assembly that achieves the object of the present invention was obtained thereby.

[Treatment Example 3]

A through-air nonwoven fabric was treated with a textile oil containing potassium lauryl phosphate and mixed potassium phosphates as anionic surfactants, and sorbitan monopalminate and sorbitan esters of tallow fatty acid as nonionic surfactants, and thereafter the cellulose sulfate was attached.

The results of the hyaluronidase inhibitory activity test revealed that before storage the inhibitory activity was 50% or higher, but after storage it had dropped to less than 50%.

[Treatment Agent 4]

A through-air nonwoven fabric was treated with a textile oil containing potassium octyl phosphate and potassium dodecyl phosphate as anionic surfactants, and ethylene glycol monobutyl ether as a nonionic surfactant, and thereafter the cellulose sulfate was attached.

The results of the hyaluronidase inhibitory activity test revealed that before storage the inhibitory activity was 50% or higher, but after storage it had dropped to less than 50%.

[Treatment Agent 5]

A through-air nonwoven fabric was treated with a textile oil containing alkyl imidazolium alkyl sulfate as a cationic surfactant and polyglycerol fatty acid esters, poly ethers, polyether esters, and ethylene oxide adduct of alkanol amide as nonionic surfactants, and thereafter the cellulose sulfate was attached.

The results of the hyaluronidase inhibitory activity test revealed that even before the storage test the inhibitory activity was less than 50%.

[Treatment Example 6]

In this treatment example cellulose sulfate alone was attached to a through-air nonwoven fabric, and no other treatment was performed.

The results of the hyaluronidase inhibitory activity test revealed that even before the storage test the inhibitory activity was less than 50%.

The results of the hyaluronidase inhibitory activity test (% inhibitory activity) obtained in treatment examples 1 to 6 above are shown in Table 2 below.

TABLE 2

| | Treatment Example | | | | | |
| --- | --- | --- | --- | --- | --- | --- |
| | 1 | 2 | 3 | 4 | 5 | 6 |
| Before storage test | ≥70 | ≥70 | ≥70 | ≥60 | <10 | <10 |
| After storage test | ≥70 | ≥70 | <40 | <40 | — | — |

INDUSTRIAL APPLICABILITY

Because cellulose sulfate has antiviral properties, a fiber assembly retaining the same can be used as a sanitary material for medical uses such as masks, gowns, surgical gowns, etc., intended for antiviral applications. The fiber assembly of the present invention is not limited to the examples described above, and can be used in a variety of ways intended for antiviral applications.

The invention claimed is:

1. A fiber assembly comprising hydrophobic fibers hydrophilized with an anionic surfactant comprising a phosphate ester salt, wherein the fiber assembly further retains cellulose sulfate and comprises pH buffer attached to the fiber assembly after the cellulose sulfate is retained thereon, the pH buffer is citrate buffer and is attached to the fiber assembly in an amount range from 0.1 to 0.2 wt % as an amount of attached components of the pH buffer relative to a total weight of the fiber assembly, the surfactant is attached to the fiber assembly in a range from 0.2 to 2.0 wt % relative to the total weight of the fiber assembly, the phosphate ester salt is a mixture of octyl phosphate salt or dodecyl phosphate salt with dipotassium tridecan-1-yl phosphate, hydrophobic fibers are, or a fiber assembly containing hydrophobic fibers is, hydrophilized with the surfactant by an immersion method, a coating method, or a spray method, so as to form the hydrophilized fibers, and the fiber assembly has a hyaluronidase inhibitory activity of 70% or higher.

2. The fiber assembly according to claim 1, wherein the fiber assembly containing the hydrophobic fibers is hydrophilized by the immersion method.

3. The fiber assembly according to claim 1, wherein the hydrophobic fibers are, or the fiber assembly is, hydrophilized in an aqueous solution of the surfactant by the immersion method.

4. The fiber assembly according to claim 1, wherein the cellulose sulfate has a degree of sulfur esterification of the cellulose sulfate in a range of 13 to 17% by weight as a sulfur concentration relative to a total amount of the cellulose sulfate.

5. The fiber assembly according to claim 1, wherein fibers constituting the fiber assembly comprise polyolefin, polyester, or a combination thereof.

6. A textile product obtained using the fiber assembly according to-claim 1.

7. A process for producing a fiber assembly comprising hydrophobic fibers hydrophilized with an anionic surfactant that comprises a phosphate ester salt, and having a hyaluronidate inhibitory activity, the process comprising:

treating a fiber assembly with an aqueous cellulose sulfate solution and drying; and then treating the fibers with a pH buffer and drying, wherein hydrophobic fibers are, or a fiber assembly containing hydrophobic fibers is, hydrophilized with the surfactant by an immersion method, a coating method, or a spray method, so as to form the hydrophilized fibers, the surfactant is attached to the fiber assembly in a range from 0.2 to 2.0 wt % relative to the total weight of the fiber assembly, the phosphate ester salt is a mixture of octyl phosphate salt or dodecyl phosphate salt with dipotassium tridecan-1-yl phosphate, the fiber assembly further retains cellulose sulfate and comprises pH buffer attached to the fiber assembly after the cellulose sulfate is retained thereon, the pH buffer is citrate buffer and is attached to the fiber assembly in an amount range from 0.1 to 0.2 wt % as an amount of attached components of the pH buffer relative to a total weight of the fiber assembly, and the fiber assembly has a hyaluronidase inhibitory activity of 70% or higher.

8. The process for producing a fiber assembly according to claim 7, wherein the fiber assembly comprises the hydrophilized hydrophobic fibers and is formed by treating the fiber assembly with the surfactant before treating the fiber assembly with the aqueous cellulose sulfate solution.

* * * * *